United States Patent [19]
Carlson et al.

[11] Patent Number: 5,612,490
[45] Date of Patent: Mar. 18, 1997

[54] METHOD AND APPARATUS FOR MEASURING PHASES IN EMULSIONS

[75] Inventors: Edwin D. Carlson, Sparta; Salvatore J. Rossetti, Bernardsville, both of N.J.

[73] Assignee: Exxon Research and Engineering Company, Florham Park, N.J.

[21] Appl. No.: 551,077

[22] Filed: Oct. 31, 1995

[51] Int. Cl.$^6$ .......................... G01N 9/26; B01D 17/06; C02F 1/40; G01R 27/22
[52] U.S. Cl. .................. 73/61.43; 210/610; 210/708; 210/799; 210/DIG. 5; 324/640; 324/694
[58] Field of Search ................ 73/61.43, 61.44; 210/610, 702, 708, DIG. 5, DIG. 6, 799; 324/640, 694

[56] References Cited

U.S. PATENT DOCUMENTS

| | | | |
|---|---|---|---|
| 4,200,550 | 4/1980 | Scherrer et al. | 252/335 |
| 4,289,020 | 9/1981 | Paap | 73/61.1 R |
| 4,774,680 | 9/1988 | Agar | 364/550 |
| 4,801,863 | 1/1989 | Schimion et al. | 324/61 R |
| 4,947,127 | 8/1990 | Helms et al. | 324/640 |
| 5,101,163 | 3/1992 | Agar | 324/639 |
| 5,101,367 | 3/1992 | Agar | 364/551.01 |
| 5,219,471 | 6/1993 | Goyal et al. | 210/787 |
| 5,234,012 | 8/1993 | Marrelli | 137/2 |
| 5,260,667 | 11/1993 | Garcia-Golding et al. | 324/694 |
| 5,341,100 | 8/1994 | Taylor | 324/341 |
| 5,363,696 | 11/1994 | Cardellini et al. | 73/61.44 |
| 5,394,339 | 2/1995 | Jones | 364/510 |
| 5,411,665 | 5/1995 | Scraggs et al. | 210/610 |
| 5,417,107 | 5/1995 | Biencourt et al. | 73/61.44 |

*Primary Examiner*—Hezron E. Williams
*Assistant Examiner*—J. David Wiggins
*Attorney, Agent, or Firm*—Edward M. Corcoran; Roy J. Ott

[57] ABSTRACT

A profile of the emulsion pad, the oil continuous and the water continuous phases present in a coalescer, such as a crude oil dehydrater or desalter, which contains sample withdrawing means such as trycocks or a swing arm sampler for withdrawing liquid samples from a plurality of known vertical positions inside the unit, is readily obtained by withdrawing samples from a plurality of known vertical positions inside the unit and passing the samples to a receiver outside the unit which contains means for measuring an electrical property determinative of the type of phase being measured and its water content. The measured electrical property may be the energy absorption of the sample, such as RF energy absorption.

12 Claims, 2 Drawing Sheets

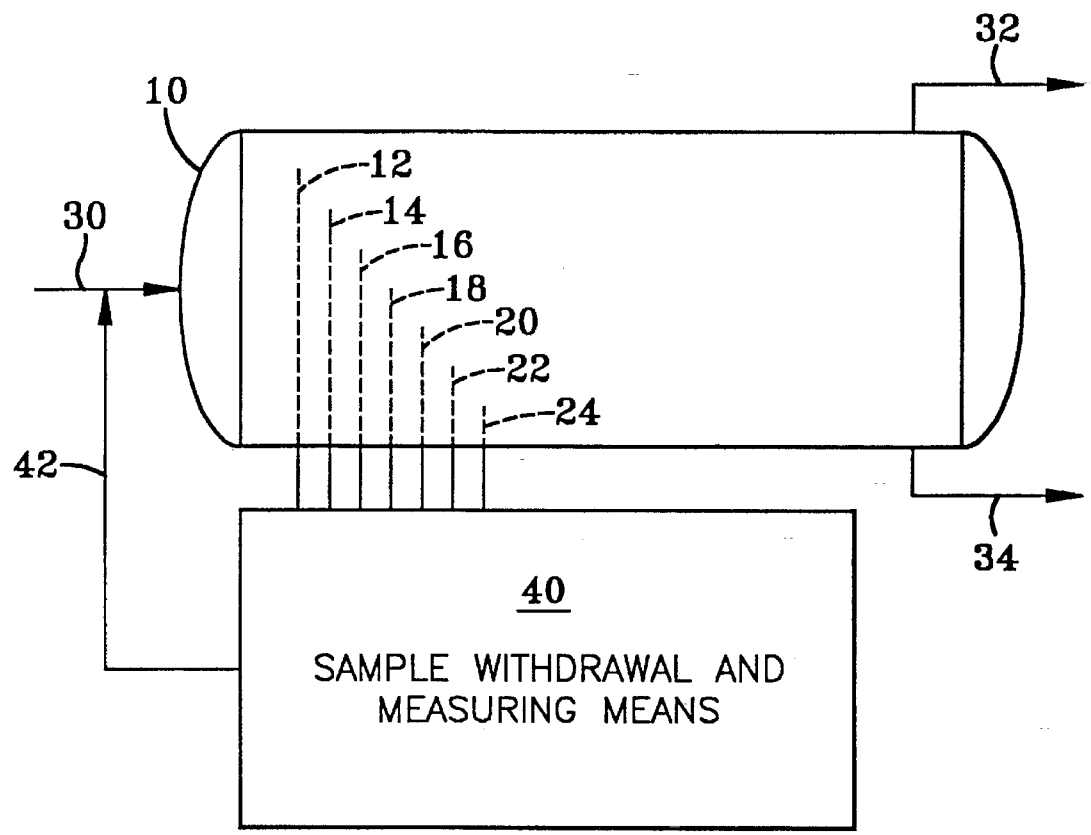
FIG-1(a)
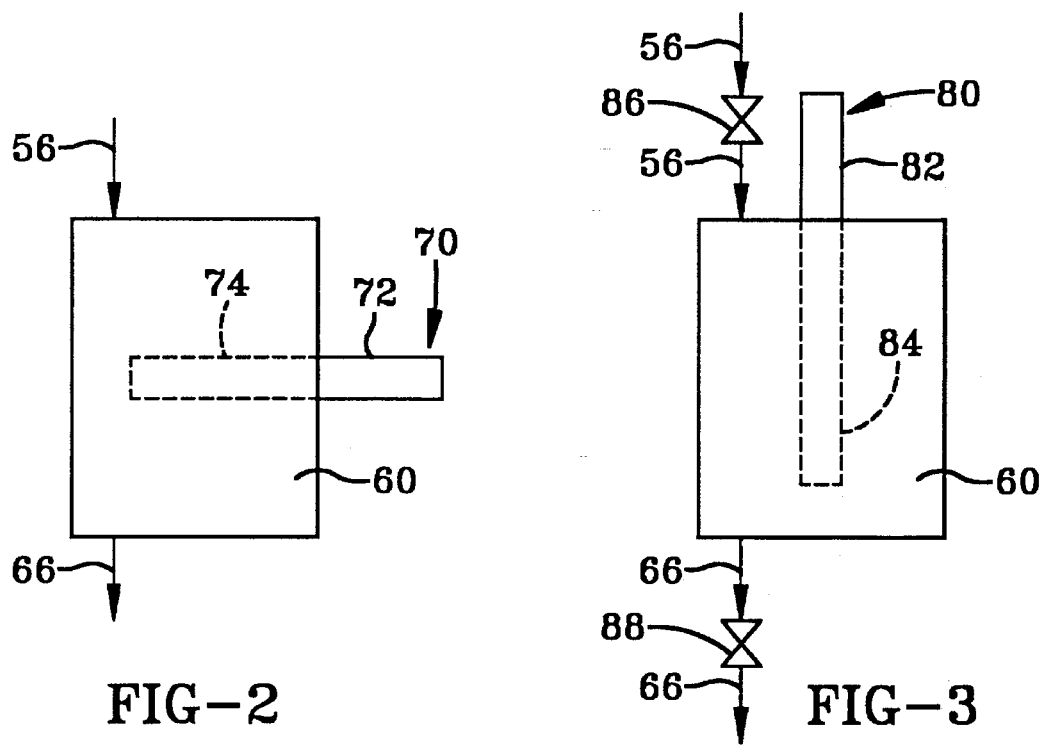
FIG-2
FIG-3

METHOD AND APPARATUS FOR MEASURING PHASES IN EMULSIONS

BACKGROUND OF THE INVENTION

1. Field of the Invention

This invention relates to a method and apparatus for measuring phase levels, interfaces and compositions in petroleum desalters and dehydrators by using sampling means in the unit to withdraw liquid samples from a plurality of known vertical levels inside the unit and passing each sample outside where an electrical property of each sample is measured which determines the water content of the sample.

2. Background of the Disclosure

Crude petroleum contains impurities which include water, salts in solution and solid particulate matter that will corrode and build up solid deposits in refinery units. These impurities must therefore be removed from the crude oil before the oil can be processed in a refinery. The impurities are removed from the crude oil by a process known as "desairing", in which hot crude oil is mixed with water and a suitable emulsifying agent to form a water-in-oil emulsion which provides intimate contact between the oil and water. The salts pass into solution in the water. The emulsion is then passed into a high voltage electrostatic field inside a closed vessel known as a desalter. The electrostatic field coalesces and breaks the emulsion into an oil continuous phase and a water continuous phase. The oil continuous phase rises to the top to form the upper layer in the desalter from where it is continuously drawn off and the water continuous phase (commonly called "brine") sinks to the bottom from where it is continuously removed. Similar equipment (or units) and procedures, except for the addition of water to the oil, are used in oil producing fields to dehydrate the oil before it is transported to a refinery. These units are referred to as electrostatic treaters, dehydrators and precipitators. This is because all crude oil pumped up from wells contains water and buyers do not want to pay for transporting, storing and pumping water or overloading desalters at the refineries.

During operation of such units, an emulsion phase of variable composition and thickness exists at the interface of the oil continuous phase and the water continuous phase in the unit. If the emulsion phase gets too thick, the oil continuous phase will contain too much brine and the lower brine phase will contain unacceptable amounts of oil. In extreme oases it results in emulsion being withdrawn from the top or bottom of the unit. Oil entrainment in the water phase is a serious problem as it is environmentally impermissible and very expensive to remedy outside the unit. Also, in many units it is desirable for the water continuous or brine phase to be as close as possible to the high voltage electrodes in the unit without resulting in shorting across the oil to the water, in order to achieve maximum coalescence of any remaining oil droplets entrained in the water continuous phase and thereby ensure that the withdrawn water phase is substantially oil free. If the emulsion phase gets too thick a demulsifying agent must be added. If the water continuous phase gets too high or too low, the water phase withdrawal valve at the bottom of the unit called a "dump valve" must be correspondingly opened or closed to the degree necessary to reposition the water phase to the desired level in the unit, and/or the oil withdrawal valve at the top of the unit correspondingly adjusted. Therefore it is necessary to monitor the level and condition of the phases in the unit.

This has traditionally been done manually by operators periodically opening trycock valves to withdraw samples from fixed levels inside the desalter. A trycock valve is merely a sample line comprising a pipe located at a fixed level in the unit, which is connected to a valve outside the unit. Some desalters have what is called a "swing arm" sample line in the unit in place of, or in addition to, trycock valves. A swing arm sample line is a pipe inside the unit open at one end for withdrawing samples, with the vertical position of the opening inside the unit manually adjusted by suitable means, such as a crank and gear mechanism outside the unit. In either case, an operator opens a sample valve to withdraw a sample and runs it over a smooth surface such as metal to visually determine if the withdrawn phase is oil or water continuous or if it is a stable emulsion phase. No quantitative information is available using this method and, further, because desalters typically operate at inside temperatures and pressures ranging between about 200° to 300° F. and 100 to 250 psi (dehydrators typically run at lower temperatures and pressures), there is a danger of the sample flashing and burning the operator. Also, the withdrawn sample may be different in phase identity at the reduced temperature and pressure outside the unit than it is inside the unit. Other methods have included the use of a float level to indicate the level of the water phase and also the use of a capacitance probe, some of which can give information about the water content of an oil phase, while others merely indicate if the phase is oil or water continuous.

Newer techniques have been introduced which employ means permanently mounted at a fixed position inside the unit for measuring an electrical property, such as energy absorption, of the fluid inside the unit. Some of these electrical means employ a probe which is able to determine the water concentration in the liquid phase surrounding the probe. In order to employ such devices in the desalter, the desalter must be drained, opened up and special nozzles and other devices welded to it. The welds require expensive post weld heat treatment. Moreover, it is simply not possible to shut down an entire refinery to modify a desalter. Consequently, any modifications must wait for a refinery turn around which can take five years or more. Furthermore, welding the devices at fixed positions on the desalter provides data only at those positions. Economic considerations prohibit the use of sufficient probes to obtain a profile of the conditions inside the desalter. Typically a probe is installed at the vertical mid-position of the drum and sometimes at an angle to try to obtain information around the mid point. Optionally, a second probe is installed near the oil outlet at the top of the unit as an emulsion carry-over alarm and a third at the brine outlet on the bottom as an oil carry-under alarm. The desalter is controlled by trying to maintain a certain water concentration at the single mid-level probe, with the outlet probes expected to serve as carry-over alarms.

SUMMARY OF THE INVENTION

The present invention relates to the discovery that the levels of the oil and water continuous phases and the water content of these phases present in a desalter, a dehydrater and other emulsion handling units or equipment can be determined by using existing sampling means inside the unit to withdraw liquid samples from a plurality of vertical levels or positions and pass each sample to at least one sample chamber outside the unit in which an electrical property determinative of the water content and phase of the sample is measured. By using the sampling means already inside the unit, there is no need to wait for a refinery turn around and also no need to weld means for determining an electrical property to the unit. By existing sampling means is meant existing trycock valves and/or a swing arm sample line, and equivalents. Since most desalters contain at least five or six trycock valves and/or a swing-arm sample line, this means that samples can be taken from a plurality of vertical levels in the desalter to obtain a vertical profile of the phases and phase levels inside in the practice of the invention. This permits more efficient operation of the unit. This is not obtainable even with prior art units containing two or three means inside the unit for measuring an electrical property of the sample as set forth above. In the case of an electrostatic coalescer, such as a desalter or dehydrator, and also for other similar emulsion handling equipment, analysis of the phase levels and their water contents permits increasing or decreasing the withdrawal rate of the water or oil continuous phases, as well as the introduction of more or less water and/or chemicals (e.g., demulsifiers and defoamers) into the emulsion of crude oil and water being fed into the unit, to achieve maximum purification of the crude oil and essentially no oil entrained in the water phase or water in the oil phase being withdrawn. Thus those skilled in the art appreciate that the oil continuous phase, the water continuous phase and the emulsion phase exist in a multilayered arrangement of said phases in which the boundaries between the phases are in a state of quasi equilibrium. Still further, in marked contrast to the prior art which employs a plurality of means for measuring an electrical property of the liquid in the unit, only one such means is needed in the practice of the invention, as will be explained under the detailed description below.

The electrical properties of the samples are measured in one or more sample chambers or receivers located outside the unit in which the sample is preferably at the same temperature and pressure existing inside the unit. The measured sample is then passed back into the desalter, so that there is no need for sample disposal. Sample withdrawal is accomplished either manually or automatically. By electrical property is meant an electrical property which measures whether the sample is oil or water continuous and, in a preferred embodiment, also provides the water content or concentration in the sample. An electrical property suitable for use in the practice of the invention includes the electrical energy absorption of the sample as measured, for example, by the strength of a high frequency [such as a radio frequency (RF)] signal transmitted through the sample from a transmitter to a receiver; by the dielectric constant of the sample; by the electrical conductivity of the sample, particularly when measured at a high frequency (such as RF); by the sample's admittance and/or impedence, and by combinations of these properties as is known in the art and disclosed, for example, in U.S. Pat. Nos. 4,774,680, 5,101, 163 and 5,101,367, the disclosures of which are incorporated herein by reference. As used herein, the term "electrical properties" includes all such properties employed singly or in combination. Means for measuring these properties in connection with both oil and water continuous phases of oil and water mixtures and emulsions are commercially available, and will be further explained with respect to their use in the present invention in the detailed description below.

In one sense the invention relates to a method for determining the level of a polar liquid continuous phase in emulsion handling equipment which contains a polar liquid continuous phase and a nonpolar liquid continuous phase and which also contains means for withdrawing liquid samples from within the equipment and passing the samples outside the equipment for measurement, said method comprising:

(a) withdrawing a liquid sample from a known level within said equipment and passing it outside said equipment, and (b) contacting said withdrawn sample outside said equipment with means which measures an electrical property of said sample to determinine if said sample is a polar liquid continuous phase.

Steps (a) and (b) are repeated as many times as desired by using the existing sample withdrawal means in the equipment to withdraw additional samples from different known vertical positions or levels in the unit and thereby obtain a profile of the phase levels in the unit. In a preferred embodiment, the measured electrical property is also determinative of the water content or concentration of each phase or sample measured and indicates whether the sample being measured is a polar or nonpolar liquid continuous phase.

With specific reference to a coalescer, such as a crude oil dehydrater or desalter which contains a water continuous phase, an oil continuous phase, an emulsion phase and liquid sampling means comprising trycocks, a swing-arm sampler, or both for withdrawing liquid samples from a plurality of known vertical levels in said coalescer and passing said samples outside of said coalescer, the invention relates to a method for determining the level of at least the water continuous phase present, said method comprising:

(a) withdrawing a liquid sample from a known level within said coalescer and passing it outside said coalescer;

(b) contacting said withdrawn sample outside said coalescer with means which measures an electrical property of said sample to determine if said sample is a water continuous phase, and (c) repeating steps (a) and (b) a desired number of times so that a plurality of samples are withdrawn and measured, with each sample being withdrawn from a different known vertical level in said coalescer.

In further embodiments said measuring means also determines if said sample is an oil continuous phase or an emulsion and also the water content of each sample. In a still further embodiment of the invention, the measured electrical property is fed to means, such as a computer, for making any necessary changes to the desalter operation by increasing or decreasing the withdrawal rate of the bottom, water continuous phase or brine, the oil continuous upper phase; the oil being fed into the coalescer, or the water and any chemicals added to the coalescer. In yet another embodiment, the invention relates to an apparatus for determining the levels of the oil and water continuous phases, and also preferably the water content or concentration of these phases. In this embodiment the apparatus comprises means for withdrawing samples from a plurality of levels in the coalescer and means outside the coalescer for measuring an electrical property determinative of whether the sample is oil or water continuous. Further embodiments include means for automatically opening and closing the sample withdrawal valves, such as valve actuation and/or computer means to automatically withdraw samples and to make any desired changes to the desalter operation based on the measured properties of the withdrawn samples.

BRIEF DESCRIPTION OF THE DRAWINGS

FIGS. 1(a) and 1(b) are simple block diagrams which schematically illustrate a desalter containing trycocks and an apparatus of the invention, respectively.

FIG. 2 schematically illustrates an embodiment of the invention using an RF emitting probe in a sample receiver.

FIG. 3 schematically illustrates an embodiment of the invention using a capacitance probe in a sample receiver.

DETAILED DESCRIPTION

Figure 1B:
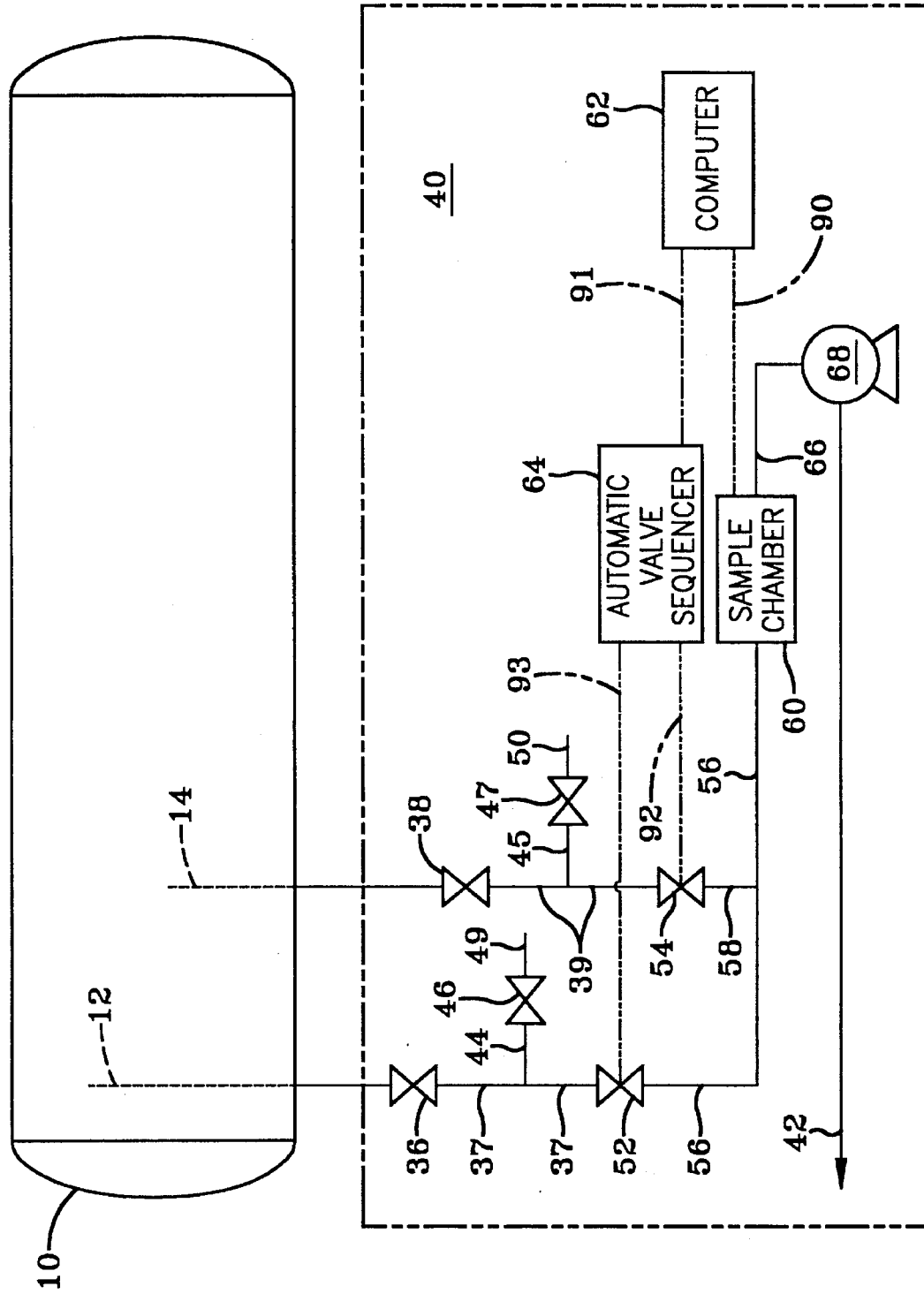

The practice of the invention is now explained in more detail with specific reference to a crude oil desalter as an illustrative, but nonlimiting example. The existing sampling means in a desalter are what is known in the art as either "trycock valves", a "swing arm sampler" or both. A trycock valve is simply a pipe open at one end inside the desalter with the open end permanently positioned at the desired vertical position or level in the desalter for withdrawing liquid samples at that level. The sample pipe runs outside the desalter where it is connected to a sample valve. There are generally five, six, or more such sample pipes in a desalter, each with its own sample valve, with the open end of each pipe at a different vertical position inside the unit, so that liquid samples can be withdrawn from a plurality of fixed vertical positions in the unit. As with a trycock valve, a swing arm sampler is a pipe with an open end inside the desalter connected to a sampling valve outside the unit. It differs from a trycock valve in that it includes means for permitting an operator to manually change the vertical position of the open end of the pipe in the desalter, by moving it up and down, so that liquid samples can be withdrawn from any desired vertical position (typically below the lowest electrode in an electrostatic coalescer such as a desalter) in the unit.

Each sample valve outside the unit is opened either automatically or manually by an operator. In the prior art, the sample exits into ambient conditions, thereby instantly depressuring the sample and often destroying the identity of the phase. This procedure can also result in the operator being burned by the hot sample. In the practice of the invention a liquid sample is automatically or manually withdrawn from the desalter by means of a trycock valve or a swing arm sampler in the unit by opening the respective sample valve outside the unit. In the practice of the invention, instead of passing the sample into the ambient, the liquid sample is fed into a sample receiver in which an electrical property of the sample is measured. Although the sample may be cooled prior to the measurement, it is preferred that the sample in the receiver is kept at the same temperature and pressure that exists in the desalter to maintain the integrity of the phase being measured. The sample receiver contains means for measuring an electrical property of the sample as defined above which is determinative of whether the sample being measured is oil or water continuous. In a preferred embodiment the measured electrical property also determines the water concentration in the sample. It is also preferred that the sample pass from the sample receiver in which it has been measured, back to the desalter. In this manner the problem of sample disposal is eliminated, the sample can flow through the receiver as At is being measured and be at the same temperature, pressure and emulsion state in the receiver in which it exists in the desalter. This is readily accomplished by a closed pipe loop which includes the sample receiver, return pump and desalter. In a further embodiment the measured electrical property of the sample is fed to means such as an automatic valve sequencer and computerized data acquisition and control system for automatically opening and closing the sampling valves and/or adjusting the height of the swing arm sampler to take and measure an electrical property of samples from a plurality of vertical positions or levels in the desalter, and using the results of these measurements to make any necessary changes in the operation of the desalter. As set forth above, these changes can include increasing or decreasing the withdrawal rate of: the bottom, water continuous phase or brine, the oil continuous upper phase, the oil being fed into the desalter or the water and emulsifier/demulsifier added to the desalter, or the incoming oil emulsion being treated. Taking samples from a plurality of vertical levels in the desalter provides information as to the height and nature of the phases (e.g., water or oil continuous phase, a stable or unstable emulsion phase), the level of such phases in the desalter, and preferably the water content of each phase. This information is then used to manually, or automatically make adjustments, if needed, to the incoming crude oil emulsion rate, the withdrawal rate of the oil or water continuous phase or to introduce more or less water, emulsifier or demulsifier into the crude oil emulsion being fed into the desalter.

Referring now to FIG. 1(a), a crude oil containing water and emulsifier as a water-in-oil emulsion is schematically illustrated as being fed into desalter drum 10 via line 30. The electrodes inside the drum, the high voltage power supply and means for coupling the voltage to the electrodes are not shown for the sake of convenience. The treated and demulsified oil continuous phase is withdrawn from the top of drum 10 via line 32, while the water continuous phase or effluent brine is withdrawn from the bottom of the drum via line 34. Drum 10 is shown as containing seven trycock sample lines 12 through 24 inside of the drum for taking liquid samples from seven different vertical positions within the drum. Sample lines 12 through 24 are permanently mounted in drum 10 and are connected by valves external of the drum (not shown) to manual sample taps (not shown) which enable an operator to manually operate the sample valves, take samples and visually determine whether the particular sample withdrawn from a particular location is an oil or water continuous phase, a stable emulsion which needs to be demulsified, and sometimes a very rough, qualitative indication of the water content of the sample. Box 40, which is illustrated in detail in FIG. 1(b) and described below, contains means according to the practice of the invention for measuring an electrical property of a liquid sample and returning the measured sample back to the desalter via lines 42 and 30. As set forth above, the desalter drum may contain a swing arm sampler in place of, or in addition to, the trycocks. Since a manually withdrawn sample is visually inspected by an operator external of the desalter and desalter environment according to the prior art method of running a sample over a smooth surface such as metal, glass or even over the side of the desalter, the sample, being at ambient or nearly ambient conditions, often no longer has the structural characteristics it had in the desalter. Therefore, the prior art manual method is often misleading with regard to the state of the emulsion and qualitative assessment of the water content. In marked contrast, the practice of the present invention provides a quantitative measurement of the water content of the sample at desalter conditions and this is related to whether the sample is an oil-in-water emulsion, a water-in-oil emulsion or a stable emulsion phase (sometimes referred to as the emulsion pad) which needs to be broken for the desalter to function effectively. Inasmuch as samples may be taken from a plurality of different vertical positions within the desalter in the practice of the invention, the state and the size or level of the phases in the unit is quantitatively determined.

FIG. 1(b) is a schematic of an embodiment of the invention shown as box 40 (sample withdrawal and measuring means) in FIG. 1(a), along with desalter drum 10 illustrated with only two of the trycocks 12 and 14 for the sake of brevity, as it is not necessary to show all of the trycocks in order to describe this aspect of the invention. Also shown in connection with the desalter are sampling valves 36 and 38 located outside the desalter for enabling an operator to manually withdraw liquid samples from inside the desalter by means of respective trycocks 12 and 14 and sample outlet lines 37 and 39. In the practice of the invention, new manual sampling taps indicated as lines 44 and 45, valves 46 and 47, and lines 49 and 50, are connected to the existing sample pipes or lines 37 and 39 exterior of the desalter as shown. Also connected to sample lines 37 and 39 are remotely operated valves 52 and 54. In this configuration original manual sample valves 36 and 38 are left permanently open, or they may be removed and discarded if desired. When a remotely operated sampling valve is opened, such as valve 52, it permits a liquid sample of the contents or phase, taken from a specific known level or height in the desalter to flow through line 56 and into sample receiver 60 which contains means (not shown) for measuring an electrical property of the sample as it flows through the receiver. The receiver can be an enclosed chamber, a pipe or other conduit having a valve at each end for receiving a sample which is measured and the sample discarded or returned to the desalter. It is preferred to use the embodiment wherein the measured sample is returned to the desalter drum. The receiver can be closed off after receiving a sample for measurement or the sample being withdrawn from the desalter drum can be permitted to continuously flow through the receiver and back into the drum as it is being measured. This is a preferred method of the practice of the invention. Also preferred in the practice of the invention is the use of only one receiver and concomitantly the use of only one means associated with the sample chamber for measuring an electrical property of the sample. The sample measuring means provides an electrical output described below, which either directly or indirectly indicates the concentration of water in the sample. The sampling valves 52 and 54, and the other sampling valves connected to respective trycocks which are not shown in FIG. 1(b), are automatically opened and closed as required by means such as a computer 62 and/or an automatic valve sequencer 64. As shown in the embodiment in FIG. 1(b), an electrical signal generated by the means measuring an electrical property of the liquid sample in receiver 60 is fed via suitable means, such as electrical wiring, cable or conduit 90, to a means 62 (such as an electronic circuit or computer and associated display means) which analyzes the signal, provides a visual indication of the type of phase and its water content and generates a signal which is fed via line 91 to an automatic valve opening means 64 which automatically opens and closes sample valves 54 and 52 by means of electrical connections illustrated by dashed lines 92 and 93, according to a predetermined sequence and/or in response to the signal (s) received from 62. In one embodiment, valve opening means 64 or other means (not shown) actuates other valves (not shown) for changing the flow rate of the oil and/or brine being removed from the desalter and for providing any chemical dosage required as a result of the measurement of the liquid sample(s) withdrawn and measured. The measured sample is returned to the desalter drum via line 66, pump 68 and sample return line 42. On desalters that use a movable internal sampling device such as a swing arm, instead of trycocks, the application of the invention is modified to include means for manipulating the level of the device in the desalter and for indicating the level at which the sample is being withdrawn. Either manual or electronic evaluation of the electrical output is used to determine the water content or concentration of each sample. Some, but not all, electrical property measuring means, such as those which measure only capacitance or conductivity are not able to discern the oil content of a water continuous phase and read the sample as being water. In this case the means is used to determine the level of the water continuous phase in the desalter.

An automatic valve opening and closing means, such as an automatic valve sequencer and computerized data acquisition and control system is used to open the sample valves to withdraw liquid samples from the desired vertical positions in the desalter for evaluation, recommend any changes in the desalter operation and, if desired, to make any required changes to the operating parameters of the desalter. Irrespective of the use of such automation, manual sample withdrawing means as illustrated in FIG. 1(b) may also be used. It is prudent for the practitioner to install manual sampling means as a back-up for an automated means. Referring again to FIG. 1(b), if manual means is installed either by itself or as a back-up, the manual sample withdrawal lines 49 and 50 are each connected by respective valves 46 and 47, lines 44 and 48 to sample lines 37 and 39 upstream of receiver 60 or to a separate receiver and concomitant means for determining the amount of water in the sample and returned to the desalter drum 10 via pump 66 and return line 42.

As stated under the Summary, means useful for measuring an electrical property of the liquid sample in the practice of the invention are commercially available. Illustrative, but nonlimiting examples include insertion type probes such as Agar probes (e.g., their OW-101) which measure the energy absorption properties of the oil/water mixture rather than just the capacitance thereof which are commercially available from the Agar Corporation in Houston, Tex.; Invalco probes available from Invalco in Hutchinson, Kans., and Drexelbrook probes available from the Drexelbrook Company in Horsham, Pa. Agar probes are available which contain high frequency or RF transmitting and receiving means mounted within the probe as a transmitting antenna and receiving element. The RF signal is generated external of the probe and electrically coupled to the probe by means such as coaxial cable or a wave guide. The fluid surrounding the probe absorbs the RF energy emitted by the antenna, with water absorbing much more energy than oil. The probe is calibrated to provide a milliamp output whose value varies linearly with the water concentration of the sample being measured. Such probes are calibrated to measure the water content or concentration of the oil/water (oil continuous phases and water continuous phases) mixture or emulsion from no water up to 100% water. Some types of probes are not able to determine the water content of an oil continuous phase containing more than 50% water and read any mixture which contains about 50% or more water as a water continuous phase. Other probes are not able to determine the water content in an oil continuous phase and tell only if the surrounding fluid is oil or water.

FIG. 2 schematically illustrates a liquid sample receiver, such as receiver 60 shown in FIG. 1(b), which contains a probe for measuring an electrical property according to the practice of the invention. In this illustration the probe is able to determine the water concentration of the oil/water emulsion or mixture from 0% water or all oil, up to 100% water and no oil. Thus, referring to FIG. 2, receiver 60 is shown with sample lines 56 and 66 [as shown in FIG. 1(b)] for the liquid sample to pass through. If desired, a static mixer (not shown) is present in the inlet line 56 just upstream of the receiver to keep the phase in its emulsified state as it enters the receiver, so that a more accurate measurement is made. An Agar probe 70 is schematically illustrated with a portion of the probe 72 outside the chamber electrically connected to means for generating the high frequency or RF signal which is emitted by the antenna portion 74 of the probe inside the chamber which is surrounded by the liquid sample being measured. Neither the signal generating meads nor the electrical coupling means is shown for the sake of brevity. RF signal receiving means (not shown) is also contained within the Agar probe and is electrically connected to means such as a meter, chart, comparator, electric circuit, computer, etc., (not shown) which provides the water concentration in the sample as a function of the output signal generated by the probe. Commercial Agar probes are available which generate a 4–20 mA output linearly proportional to the concentration of the water in the sample. Depending on the factory calibration, the 4 mA output can be set to 0% water and the 20 mA output to 100% water. These output readings are easily checked prior to installation by inserting the probe in a reference container of water and in a reference container of oil. An electronic circuit, computer or other suitable means mentioned above converts the mA output to the water concentration in the emulsion or phase being measured.

With a capacitance probe, an electrically conductive probe or plate, electrically insulated from its surroundings, acts as one plate of the capacitor. The other plate may be part of the probe or the metal wall of the metal sample receiver. The sample being measured acts as a dielectric medium. As mentioned above, a quantitative indication of the water concentration is not always available with this means. In a case in which the capacitance probe measures a water continuous phase as 100% water, the probe may still be useful with respect to the water concentration in the oil continuous phase and for indicating the level of the water continuous phase. FIG. 3 schematically illustrates a liquid sample receiver, such as receiver 60 shown in FIG. 1(*b*), but which contains a capacitance probe. Thus, referring to FIG. 3, sample receiver 60 is shown with liquid sample lines 56 and 66 [as shown in FIG. 1(*b*)] for the liquid sample to pass through the receiver. A capacitance probe 80 is schematically illustrated with a portion of the probe 82 outside the chamber electrically connected to means (not shown) for generating a current which is applied to the probe 84 inside the sample receiver 78 in which the probe is surrounded by the liquid sample being measured. In this case the probe contains both plates of the capacitor. A current or voltage output indicates whether the sample is oil continuous and, with some capacitance probes, the water concentration in the oil continuous sample. As with the Agar probe, the output is fed to means such as an automatic valve sequencer or a computer or both to make any necessary adjustments in the operation of the desalter. Isolation valves 86 and 88 are closed while making the measurement.

The practice of the invention is not limited to use with desalters and similar equipment or units, but is useful with any emulsion handling equipment having internal sampling means for withdrawing samples from a plurality of levels in the unit and passing then outside the unit to a sample receiver. It is also useful with emulsions of any two liquids having different measurable electrical properties. One example is emulsions of polar/nonpolar liquids such as acids and hydrocarbons.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all the features of patentable novelty which reside in the present invention, including all the features and embodiments which would be treated as equivalents thereof by those skilled in the art to which the invention pertains.

The invention will be further understood with reference to the examples below.

EXAMPLES

Example 1

A crude oil emulsion containing 2–8% water is fed into a desalter equipped with six trycock sample valves, each connected by liquid lines to a sample receiver containing an Agar probe. The system is equipped with automatic valve sequencer and computerized data acquisition and control systems. Valve operation is programmed to sequentially sample from each of the six trycock valves. Timing is set to allow purging of sample receiver lines prior to acquiring data on water content at the sample point. Acquired data from each cycle are analyzed using computer software to determine the level of the aqueous phase and the widths of the water-in-oil emulsion and the oil-in-water emulsion in the desalter. Based on these results, the desalter dump valve opening is automatically controlled and chemical additive rate and type are suggested for operator action.

Example 2

A crude oil emulsion containing 2–8% water is fed into a desalter equipped with six trycock sampling valves, each connected by liquid lines to a sample receiver containing a Drexelbrook capacitance probe which outputs the water level in the receiver. The system is equipped with automatic valve sequencer and computerized data acquisition and control systems. Valve operation is programmed to sequentially sample from each of the six trycock valves. Timing is set to allow purging of the sample receiver, to close the sample receiver isolation valves prior to acquiring data, and to open the isolation valves after acquiring the data. The acquired data are used to determine the aqueous phase level in the desalter and control operation of the desalter dump valve. The data are also useful in determining the depth of the water-in-oil emulsion and either control or recommend chemical additive rates.

Example 3

A crude oil emulsion containing 1–15% water is fed into a dehydrator equipped with six trycock sampling valves, each connected by liquid lines to a sample receiver containing an Agar probe. The system is equipped with a programmable automatic valve sequencer, local readout and control of the dehydrator dump valve operation. During normal operation, dump valve control is accomplished through maintaining set water concentration at one of the sample points. An operator manually activates the valve sequencer to obtain the emulsion profile in the dehydrator when desired, in the case of, for example, a problem or abnormal operation of the unit. Information acquired during profiling is used to determine chemical additive rate and type.

Example 4

A crude oil emulsion containing 2–8% water is fed into a desalter equipped with a swing arm sampling system connected by liquid lines to a sample receiver containing an Agar probe. The system is equipped with an automated motorized system to sequentially rotate the swing arm sampler to six defined vertical positions within the desalter, computerized data acquisition and analysis, and automatic control of the desalter dump valve operation. Timing is set to allow purging of the receiver and lines before acquiring any data at any of the sample points. The acquired data are used to determine and control the aqueous phase in the desalter, and the rate and type of chemical additive required to minimize the width of the oil-in-water layers in the desalter.

What is claimed is:

1. A method for determining the level of a polar liquid continuous phase in a coalescer which contains said polar liquid continuous phase, a nonpolar liquid continuous phase and an emulsion phase in a multilayered arrangement of said phases having boundaries between said phases in quasi equilibrium under known conditions of pressure and temperature, said coalescer further containing means for withdrawing liquid samples from a plurality of known vertical positions in said coalescer and passing said samples outside of said coalescer, said method comprising:

(a) withdrawing a liquid sample from a known vertical position within said coalescer via a closed conduit system and passing it outside said coalescer via said closed conduit system into a sample receiver in which said sample is at substantially the same pressure and temperature conditions in said receiver as is known for said coalescer at said known vertical position;

(b) contacting said withdrawn sample in said sample receiver with means outside said coalescer for measuring an electrical property of said sample and determining in said sample the concentration of a polar liquid phase, and (c) repeating steps (a) and (b) a desired number of times so that a plurality of samples are withdrawn and measured, with each sample being withdrawn from a different known vertical position in said coalescer.

2. A method according to claim 1 wherein said polar liquid comprises water, said nonpolar liquid comprises oil and said emulsion is an emulsion of said water and oil.

3. A method according to claim 2 wherein said measuring means also determines if said sample is an oil continuous phase.

4. A method according to claim 3 wherein said measuring means also determines the water content of each sample.

5. A method according to claim 4 wherein said measuring means determines if each sample is oil or water continuous or an emulsion phase.

6. A method according to claim 5 wherein said measured electrical property comprises electrical signal energy absorption.

7. A method according to claim 6 wherein said energy absorption comprises the absorption of an RF signal and wherein said oil comprises crude oil.

8. A method according to any of claims 1, 3, 5, 6 or 7 wherein said means for measuring said electrical property provides an output which is electrically coupled to means for automatically withdrawing and measuring said samples.

9. A method according to claim 8 wherein said automatic means makes adjustments to the operation of said coalescer based on the results of said measured electrical property.

10. A desalter comprising a desalting drum which serves as an emulsion coalescer, means for feeding an emulsion of crude oil and water into said drum and means for withdrawing an oil continuous phase and a water continuous phase from said drum, said drum further containing (i) electrostatic means for breaking said emulsion into an oil continuous phase, a water continuous phase and an emulsion phase in a multilayered arrangement of said phases in said drum having boundaries between said phases in quasi equilibrium under known conditions of pressure and temperature and (ii) liquid sampling means selected from the group consisting of trycocks, a swing-arm sampler, or having both said trycocks and said swing-arm sampler for withdrawing liquid samples from a plurality of known vertical positions in said desalter and separately passing each withdrawn sample outside of said desalter at substantially the same pressure and temperature conditions as known for the coalescer at said known vertical positions, said desalter also containing at least one sample receiver outside of said drum with said receiver containing means for measuring an electrical property of said withdrawn sample which is determinative of whether said sample is water or oil continuous and the water content of said sample.

11. A desalter according to claim 10 wherein said means for measuring said electrical property provides an output which is electrically coupled to means for automatically withdrawing and measuring said samples.

12. A desalter according to claim 11 wherein said automatic means makes adjustments to the operation of said coalescer based on the results of said measured electrical property.

* * * * *